(12) United States Patent
Goldman et al.

(10) Patent No.: US 8,003,379 B2
(45) Date of Patent: Aug. 23, 2011

(54) HIGH DENSITY BIOREACTOR SYSTEM, DEVICES, AND METHODS

(75) Inventors: Arnold J. Goldman, Jerusalem (IL); Michael Kagan, Jerusalem (IL); Yuri Kokotov, Ma'aleh Adumim (IL)

(73) Assignee: Brightsource Energy, Inc., Oakland, CA (US)

( * ) Notice: Subject to any disclaimer, the term of this patent is extended or adjusted under 35 U.S.C. 154(b) by 757 days.

(21) Appl. No.: 11/832,201

(22) Filed: Aug. 1, 2007

(65) Prior Publication Data

US 2008/0293132 A1 Nov. 27, 2008

Related U.S. Application Data (60) Provisional application No. 60/821,074, filed on Aug. 1, 2006.

(51) Int. Cl.
*C12M 1/00* (2006.01)
*C12M 3/00* (2006.01)
*A01G 7/00* (2006.01)
*A01H 13/00* (2006.01)

(52) U.S. Cl. .............. 435/292.1; 435/298.1; 435/307.1; 435/303.1; 435/290.4; 435/286.6; 435/293.1; 435/289.1; 435/294.1; 435/299.1; 47/1.4; 385/900; 385/901; 385/147

(58) Field of Classification Search .............. 435/292.1, 435/298.1, 307.1, 303.1, 290.4, 286.6, 293.1, 435/289.1, 294.1, 299.1; 47/1.4; 385/900, 385/901, 147
See application file for complete search history.

(56) References Cited

U.S. PATENT DOCUMENTS

| | | | |
|---|---|---|---|
| 3,800,761 A | 4/1974 | Sata | |
| 3,959,923 A * | 6/1976 | Selke | ................... 47/1.4 |
| 3,982,878 A | 9/1976 | Yamane et al. | |
| 4,099,381 A | 7/1978 | Rappoport | |
| 4,117,682 A | 10/1978 | Smith | |
| 4,167,856 A | 9/1979 | Seidel et al. | |
| 4,266,179 A | 5/1981 | Hamm, Jr. | |
| 4,313,304 A | 2/1982 | Hunt | |
| 4,317,659 A | 3/1982 | Down | |
| 4,365,618 A | 12/1982 | Jones | |
| 4,403,601 A | 9/1983 | Hunt | |
| 4,433,673 A | 2/1984 | Vierling | |
| 4,435,198 A | 3/1984 | Gray | |

(Continued)

FOREIGN PATENT DOCUMENTS

DE 3710611 10/1988
(Continued)

OTHER PUBLICATIONS

Cheng-Wu et al., "Characterization of Growth and Arachidonic Acid Production of *Parietochloris incisa* Comb. Nov (Trebouxiophyceae, Chlorophyta)" Journal of Applied Phycology, 2002, 14(6):pp. 453-460.

(Continued)

*Primary Examiner* — Nathan A Bowers
(74) *Attorney, Agent, or Firm* — Miles & Stockbridge P.C.; Mark A. Catan (57) ABSTRACT

A bioreactor and bioreactor system are suitable for the growth of materials from algae. More specifically, the system preferred embodiments use concentrated sunlight in a solo- or co-generation system to produce algae and products therefrom as well as solar thermal energy.

19 Claims, 5 Drawing Sheets

U.S. PATENT DOCUMENTS

| | | | |
|---|---|---|---|
| 4,512,336 A | | 4/1985 | Wiener |
| 4,589,377 A | | 5/1986 | Van Dal |
| 4,674,463 A | | 6/1987 | Duckworth et al. |
| 4,727,930 A | | 3/1988 | Bruckner et al. |
| 4,778,759 A | | 10/1988 | Szalay et al. |
| 4,841,731 A | | 6/1989 | Tindell |
| 4,952,046 A | | 8/1990 | Stephens et al. |
| 5,016,599 A | | 5/1991 | Jubb |
| 5,228,529 A | | 7/1993 | Rosner |
| 5,239,858 A | | 8/1993 | Rogers et al. |
| 5,270,175 A | | 12/1993 | Moll |
| 5,319,934 A | | 6/1994 | Parker et al. |
| 5,400,175 A | | 3/1995 | Johansen et al. |
| 5,417,052 A | | 5/1995 | Bharathan et al. |
| 5,512,480 A | * | 4/1996 | Sandstrom et al. ......... 435/289.1 |
| 5,664,414 A | | 9/1997 | Bronicki et al. |
| 5,674,064 A | | 10/1997 | Francis, Jr. |
| 5,806,317 A | | 9/1998 | Kohler et al. |
| 5,904,748 A | | 5/1999 | Ehrensberger et al. |
| 5,958,761 A | * | 9/1999 | Yogev et al. ............... 435/292.1 |
| 5,980,605 A | | 11/1999 | Yao et al. |
| 6,035,641 A | | 3/2000 | Lokhandwala |
| 6,141,949 A | | 11/2000 | Steinmann |
| 6,167,706 B1 | | 1/2001 | Bronicki et al. |
| 6,237,337 B1 | | 5/2001 | Bronicki et al. |
| 6,287,852 B1 | * | 9/2001 | Kondo et al. ............... 435/292.1 |
| 6,321,539 B1 | | 11/2001 | Bronicki et al. |
| 6,370,815 B1 | | 4/2002 | Skill et al. |
| 6,449,954 B2 | | 9/2002 | Bachmann |
| 6,477,841 B1 | | 11/2002 | Yantovsky |
| 6,510,695 B1 | | 1/2003 | Fisher |
| 6,516,794 B2 | | 2/2003 | Karni et al. |
| 6,603,069 B1 | * | 8/2003 | Muhs et al. ................... 136/246 |
| 6,610,193 B2 | | 8/2003 | Schmitman |
| 6,637,183 B2 | | 10/2003 | Viteri et al. |
| 6,694,738 B2 | | 2/2004 | Bronicki et al. |
| 6,818,239 B2 | | 11/2004 | Kagan et al. |
| 6,899,097 B1 | | 5/2005 | Mecham |
| 6,957,536 B2 | | 10/2005 | Litwin et al. |
| 6,959,993 B2 | | 11/2005 | Gross et al. |
| 7,135,332 B2 | * | 11/2006 | Ouellette ................... 435/290.1 |
| 7,191,597 B2 | | 3/2007 | Goldman |
| 7,191,736 B2 | | 3/2007 | Goldman |
| 7,192,146 B2 | | 3/2007 | Gross et al. |
| 7,231,128 B2 | * | 6/2007 | Muhs et al. ...................... 385/88 |
| 7,331,178 B2 | | 2/2008 | Goldman |
| 2002/0046561 A1 | | 4/2002 | Bronicki et al. |
| 2003/0059932 A1 | * | 3/2003 | Craigie et al. .............. 435/292.1 |
| 2003/0131582 A1 | | 7/2003 | Anderson et al. |
| 2004/0129188 A1 | | 7/2004 | Traina |
| 2004/0144338 A1 | | 7/2004 | Goldman |
| 2005/0239182 A1 | * | 10/2005 | Berzin ........................... 435/166 |
| 2005/0279095 A1 | | 12/2005 | Goldman |
| 2006/0048517 A1 | | 3/2006 | Fradette et al. |
| 2007/0012041 A1 | | 1/2007 | Goldman |
| 2007/0084208 A1 | | 4/2007 | Goldman |
| 2007/0157614 A1 | | 7/2007 | Goldman |
| 2007/0221208 A1 | | 9/2007 | Goldman |
| 2007/0289206 A1 | * | 12/2007 | Kertz ............................... 47/1.4 |
| 2008/0000436 A1 | | 1/2008 | Goldman |
| 2008/0011290 A1 | | 1/2008 | Goldman et al. |
| 2008/0153080 A1 | | 6/2008 | Woods et al. |
| 2008/0176304 A1 | | 7/2008 | Lee |
| 2008/0250715 A1 | | 10/2008 | Cooper et al. |
| 2009/0155864 A1 | | 6/2009 | Bauer et al. |
| 2009/0197322 A1 | | 8/2009 | Goldman |

FOREIGN PATENT DOCUMENTS

| | | | |
|---|---|---|---|
| EP | 0640794 | | 2/2001 |
| GB | 2235210 A | * | 2/1991 |
| WO | WO 2004/067933 | | 8/2004 |
| WO | WO 2007/070452 A1 | | 6/2007 |
| WO | WO 2007/118223 | | 10/2007 |
| WO | WO 2008/118980 | | 10/2008 |
| WO | WO 2008/128237 | | 10/2008 |
| WO | WO 2008/154599 | | 12/2008 |
| WO | WO 2009/015219 | | 1/2009 |
| WO | WO 2009/015388 | | 1/2009 |

OTHER PUBLICATIONS

Choi et al., "Evaluation of Factors Promoting Astaxanthin Production by a Unicellular Green Alga, Haematoccus pluvialis with Fractional Factorial Design," Biotechnology Progress, 2002, 18(6):pp. 1170-1175.

Hata et al., "Production of Astaxanthin by Haematococcus pluvialis in a Sequential Heterotrophic-photoautotrophic Culture," Journal of Applied Phycology, 2001, 13(5):pp. 395-402.

Hejazi et al, "Milking Micro Alga Duneliella salina for Beta Carotene Production in Two-Phase Bioreactors," Biotechnology & Bioengineering, 2004, 85(5):pp. 475-481.

Kobayashi et.al., "Effects of Light Intensity, Light Quality, and Illumination Cycle on Astaxanthin Formation in Green Alga, Haematococcus pluvialis," Journal of Fermentation and Bioengineering, 1992, 74:61-63.

Kobayashi et al., "Growth and asta-xanthin formation of Haematococcus pluvialis in heterotrophic and mixotrophic conditions," Journal of Fermentation and Bioengineering, 1992, 74:pp. 17-20.

Lee et al., "Accumulation of Astaxanthin in Haematococcus lacustris (Chlorophyta)," Journal of Phycology, 1991, 27(5):pp. 575-577.

Leon et al., "Microalgae Mediated Photoproduction of Beta Carotene in Aqueous-organic Two Phase Systems," Biomolecular Engineering, 2003, 20(4-6):pp. 177-182.

Marquez et al., "Growth Characteristics of Spirulina platensis in Mixotrophic and Heterotrophic Conditions," Journal of Fermentation and Bioengineering, 1993, 76(5):pp. 408-410.

Martin et al., "Engineering a mevalonate pathway in Escherichia coli for production of terpenoids," Nature Biotechnology, Jul. 2003, 21(7): pp. 796-802.

Ogawa et al., "Bioenergetic Analysis of Mixotrophic Growth in Chlorella vulgaris and Scenedesmus acutus," Biotechnology & Bioengineering, 1981, 23(5):pp. 1121-1132.

Park et al., "Astaxanthin Production of Haematococcus pluvialis Under Various Light Intensities and Wavelengths," Journal of Microbiology and Biotechnology, 2001, 11(6):pp. 1024-1030.

Richmond, A. (editor), Handbook of Microalgal Culture: Biotechnology and Applied Phycology, Blackwell Publishing, 2004, pp. 456-470.

Zhang et al., "Kinetic Models for Astaxanthin Production by High Cell Density Mixotrophic Culture of the Microalga Haematococcus pluvialis," Journal of Industrial Microbiology and Biotechnology, 1999 23(1):pp. 691-696.

Barbera et al., "Modelling Mixotrophic Growth of Microalgae: Haematococcus lacustris," Afinidad, 2002, 59(500): pp. 386-390.

Ashkenazi, R., "The Response of Dunaliella bardawil to the Natural Changes in the Sunlight Spectrum and Intensity," Weizmann Institute of Science, PhD Dissertation, Sep. 1999.

Tekoah, Y., "The Effects of the Spectrum and Concentration of Light on the Productivity of Microalgae," Weizmann Institute of Science, Master of Science Thesis, Nov. 1994.

Dunahay et al., "Manipulation of Microalgal Lipid Production Using Genetic Engineering," Applied Biochemistry and Biotechnology, Mar. 1996, 57-58(1):pp. 223-231.

Nakas et al., "System Development for Linked-Fermentation Production of Solvents from Algal Biomass," Applied and Environmental Microbiology, Nov. 1983, 46(5):pp. 1017-1023.

Haslbeck et al., "Evaluation of fossil fuel power plants with $CO_2$ recovery," Department of Energy, Feb. 2002, p. 3-1.

* cited by examiner

HIGH DENSITY BIOREACTOR SYSTEM, DEVICES, AND METHODS

CROSS REFERENCE TO RELATED APPLICATIONS

The present application claims the benefit of U.S. Provisional Application No. 60/821,074, filed Aug. 1, 2006, and claims priority to International Patent Application No. PCT/US07/66195, filed Apr. 6, 2007, both of which are hereby incorporated by reference in their entireties.

FIELD OF THE INVENTION

This invention relates to the growth of biomass using solar radiation and other energy sources.

BACKGROUND

The growth of biomass for use in manufacturing pharmaceuticals, human and animal foods, and gaseous and liquid fuels requires improvements in cost efficiency and land usage in order to be economically viable on a large scale. For example, soybean oil is increasingly used as a feedstock for producing biodiesel, but is often more expensive than crude oil and yields only about 60 gallons of biodiesel per acre per year.

From 1978 to 1996, the U.S. Department of Energy's Office of Fuels Development funded a program to develop renewable transportation fuels from algae. The main focus of the program, known as the Aquatic Species Program (or ASP) was the production of biodiesel from high lipid-content algae grown in ponds, utilizing waste $CO_2$ from coal fired power plants. The end result of the study was the recognition that additional work is needed in order to reduce production costs to the level where biodiesel from microalgae can compete with petro-diesel. The ASP research focused on growing organisms in open ponds (with circulation) but ignored the scientific potential of closed systems because it was believed that such systems would be too expensive to allow cost competitiveness with petroleum. Unfortunately, open-pond systems had insurmountable problems with contamination and most development efforts today are focused on closed systems. The fact that petroleum prices have risen significantly, in real terms, since the end of the ASP effort has given added impetus to the drive to develop high-volume bioreactor systems with the potential to grow biomass at low unit costs.

SUMMARY OF THE INVENTION

According to an embodiment, the invention is a photobioreactor system that has a receiver with an aperture, a solar concentrator, the receiver being positioned to receive concentrated sunlight from the concentrator through the aperture. An array of flat members has respective first surfaces. The flat members form a cascade with each being positioned and oriented to receive substantially one sun or less of solar flux or less than 1000 Watts per square meter the first surfaces through the aperture. A fluid conveyance is configured such that, by gravity, a fluid received by a first of the flat members runs down the first flat member first surface and is conveyed to a second of the flat members and runs down the second flat member first surface.

In a variation of the foregoing embodiment, the level is between ⅓ and ⅔ of a sun or between 300 and 700 Watts per square meter. In another variation, the level is about a half sun or about 500 Watts per square meter.

Preferably, the flat members are oriented at between 5 and 20 degrees from the horizontal. A control system may be configured to control the solar concentrator to regulate the intensity of flux falling on the flat member first surfaces over the course of time to maintain at least one target flux level. The flat members may be of polymeric material, for example PVC or polyethylene. The receiver may have another aperture and another array of flat members positioned and oriented to receive light through the other aperture. Preferably, the solar concentrator includes an array of heliostats surrounding the receiver.

Preferably, the receiver includes a recirculating fluid transport device that partially recirculates fluid from the bottom back to the top so that the fluid flows down the cascade of flat members and partially conveys fluid away from the receiver.

The aperture may be covered by a light transmitting wall or glazing. The wall may attenuate selected optical wavelengths or block the light altogether or a range between 0 and 100 percent blocking. Second surfaces of each flat member, located behind the first surfaces, preferably have a reflective coating or surface to reflect back to adjacent first surfaces. The surface may be a diffuse or specular reflecting surface.

The flat members may include cooling channels. The cooling channels may be aligned with the first surfaces. The first surfaces preferably have augmentation and orientations such that liquid may pool in recesses at depths of no more than 20 mm.

A fluid conveyance preferably includes a vessel with a gas supply. The fluid conveyance may also include a gas outlet. The fluid conveyance may also be coupled to a milking apparatus for removing a substance from algae, such as an oil. The solar concentrator may include a ring of heliostats in the shape of a rhombus surrounding the receiver. In an embodiment, the fluid conveyance conveys fluid consisting substantially of algae and liquid media where the dry mass of algae is 25 g. per liter of the fluid.

According to another embodiment, the invention is a photobioreactor with a receiver. The receiver has an aperture and an array of flat members forming a cascade, each being positioned and oriented to receive light transmitted through the aperture. A flux regulator is located at the aperture configured to selectively block radiation components passing through the aperture. The flux regulator may include at least one movable selective wavelength filter. A controller may control the flux regulator responsively to time of day. A controller may perform real-time control of the flux regulator responsively to at least one measured property of sunlight.

According to another embodiment, the invention is a photobioreactor system with a receiver having an aperture, and a solar concentrator. The receiver is positioned to receive concentrated sunlight from the concentrator through the aperture. A fluid conveyance has surfaces and a mechanism to control the flux received on the surfaces through the aperture to a level less than one sun or about 1000 Watts per square meter. The fluid conveyance conveys fluid consisting substantially of algae and liquid media where the dry mass of algae is 25 g. per liter of the fluid. Preferably, the level is between ⅓ and ⅔ of a sun or between 300 and 700 Watts per square meter. More preferably, the level is about a half sun or about 500 Watts per square meter. In a variation, the receiver includes a recirculating fluid transport device that partially recirculates fluid from the bottom of the receiver back to the top so that the fluid flows down the flows over the surfaces and partially conveys fluid away from the receiver. In another variation, the receiver includes a recirculating fluid transport device that partially recirculates fluid from the bottom of the receiver back to the top so that the fluid flows down the flows over the surfaces.

According to an embodiment, the invention includes a photobioreactor system, with a receiver having an aperture. The receiver is configured to receive light through the aperture. An array of flat members with variegated surfaces forms recesses and peaks, the flat members being positioned to receive light on the variegated surfaces when transmitted through the aperture. A fluid conveyance includes the flat members configured such that, by gravity, a fluid received by a first of the flat members runs down the first flat member first surface and is conveyed to a second of the flat members and runs down the second flat member first surface. The variegated surfaces are configured such that fluid pools in at least some of them at a depth of 20 mm or less.

In a variation of the foregoing embodiment, the difference in depth between the recesses and peaks is about 20 mm. The flat members may be oriented at between 5 and 20 degrees from the horizontal. The flat members are of polymeric material, metal, or ceramic or any other suitable material. The receiver may have another aperture and another array of flat members positioned and oriented to receive light through the another aperture.

The fluid conveyance may include a recirculating fluid transport device that partially recirculates fluid from the bottom back to the top so that the fluid flows down the cascade of flat members and partially conveys fluid away from the receiver. The aperture may be covered by a light transmitting wall. The wall may attenuate selected optical wavelengths rather than block light altogether, such as by filtering out certain frequencies. Second surfaces of each flat member located behind the first surfaces and may have a reflective coating.

The flat members may include cooling channels that conduct heat from fluid flowing along the variegated surface. The channels may also be adjacent to, or integrated into the variegated surfaces. The surface augmentation of the members may be such that liquid may pool in recesses at depths of no more than 20 mm. The fluid conveyance may including a vessel with a gas supply. The fluid conveyance may include a vessel with a gas supply and a gas outlet.

Other objects, advantages and novel features of the present invention will become apparent from the following detailed description of the invention when considered in conjunction with the accompanying drawings.

DETAILED DESCRIPTION OF THE INVENTION

A photo bio-reactor (PBR) uses light to grow a photosynthetic biomass such as a microalga. According to some embodiments of the invention, a PBR can also be used for growing non-photosynthetic organisms during periods without light, and in other embodiments can also be used for growing organisms both photosynthetically and non-photosynthetically, whether at the same time or at different times. In some embodiments, the PBR is used for autotrophic growth of organisms and in other embodiments is used for heterotrophic or mixotrophic growth. In alternative embodiments an organism capable of mixotrophic growth is photosynthetically grown in a photosynthetic phase in a PBR and transferred to a different reactor for non-photosynthetic growth in a non-photosynthetic phase.

A PBR includes external planar walls, although in alternative embodiments the walls can be non-planar, including cylindrical or spherical arcs. In exemplary embodiments, the walls are substantially liquid- and gas-impermeable, and at least one wall is substantially light-transparent. Internal surfaces are provided within the PBR and are aligned to provide more total lit biomass-producing area relative to the area of the PBR footprint than would be available without the presence of the internal surfaces.

In an embodiment, a PBR includes a plurality of angled plates upon which sunlight impinges. The sunlight can be either direct or diffuse (or both), and in other embodiments has been reflected at least once, spectrally filtered, and/or concentrated before entering the interior volume of the PBR. In another embodiment, a biomass is allowed or caused to flow into and out of a PBR. In a further embodiment, a biomass is allowed or caused to flow within a PBR.

In other embodiments, the biomass includes microalgae in a liquid medium. In some embodiments the biomass is a suspension of microalgae in a liquid medium. In an example, the microalgae are grown autotrophically and the liquid medium is water or salt water. In another example, the microalgae are grown heterotrophically and the liquid medium includes hydrocarbons and water. In yet another example, the microalgae are grown mixotrophically and the liquid medium is at times water or salt water, and at other times includes hydrocarbons and water. In preferred embodiments, the density of the biomass in terms of dry algal mass per volume of biomass is at least 20 grams per liter. In especially preferred embodiments, the density is at least 25 grams per liter.

According to an embodiment, the solar radiation entering a PBR is reflected at least once in order to obtain an even distribution of light within the PBR and to effect photoautotrophic or photoheterotrophic growth of microalgae. In another embodiment, reflected solar radiation is reflected by tracking heliostats which are optionally programmable for optimized distribution of light, regulation of temperature, or other optimization goal. In a further embodiment, reflected solar radiation is spectrally filtered or split for biomass growth maximization and/or optimized light utilization, and in another further embodiment, reflected solar radiation is concentrated, for example by a lens.

In a preferred embodiment, a plurality of angled plates in a PBR forms a cascade that allows a biomass to flow from plate to plate by gravity.

Figure 1:
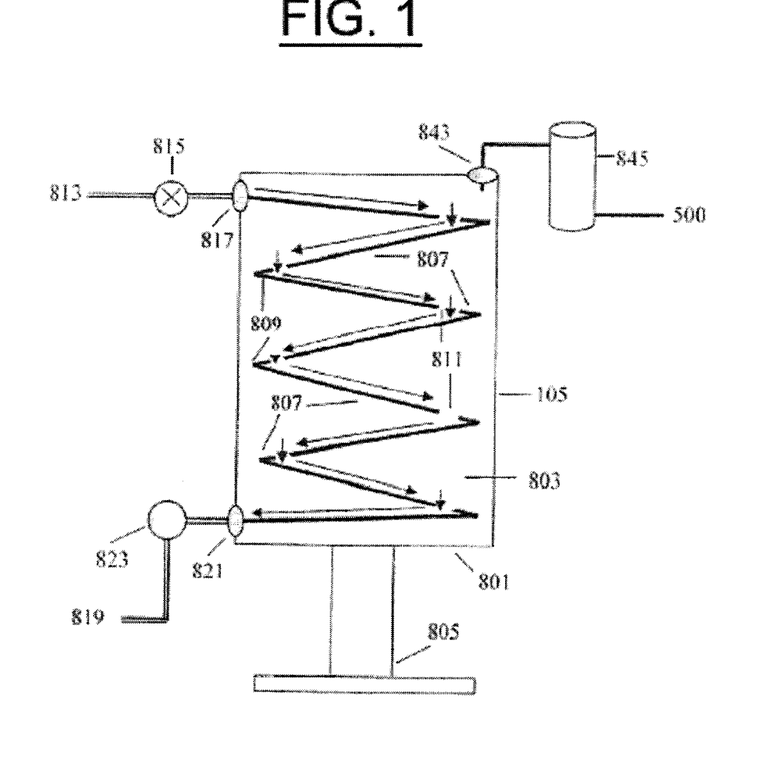
FIG. 1 is an elevation-view cross section of a photo bio-reactor, with ingress and egress elements shown schematically.

Referring now to the figures and in particular to FIG. 1, a photo bioreactor (PBR) 105 includes external walls 803 constructed of substantially liquid- and gas-impermeable materials such as glass, plastic, metal, ceramics and composites, with at least two walls 803 being substantially transparent to visible light. Examples of suitable plastics are polyethylene or polyvinyl chloride. The interior volume of the bioreactor 105 includes a zigzag or cascade arrangement of algal production plates 807. The angle 809 between each of the algal production plates 807 is determined by the required flow rate and layer thickness of the algal biomass which is in turn is a function of algal biomass viscosity and the turbulence of the biomass flow. In exemplary embodiments the angle is less than 30 degrees, and in preferred embodiments is between 5 and 20 degrees.

Algal biomass 813 flowing down the algal production plates 807 passes from plate to plate via a gap 811 in the lower end of the algal production plates 807. The presence of the gap 811 causes a waterfall effect as the algal biomass traverses from algal production plates 807 to algal production plates 807. In an alternative preferred embodiment, illustrated in FIG. 2, biomass 1010 flows down the top side of each plate 1104 into a gutter 1102 which overflows onto the top surface of the plate below.

Figure 2:
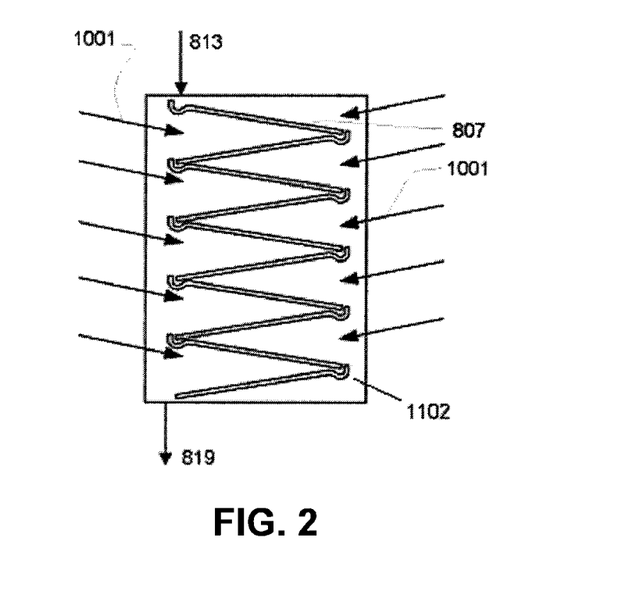
FIGS. 2 and 3 are elevation-view cross sections of photo bio-reactors.

In another alternative preferred embodiment, the plates angled in one direction are horizontally displaced relative to the plates angled in the other direction in order to create both a horizontal interval and a vertical interval between the lower end of one plate and the upper end of the plate below, allowing the algal biomass to drop turbulently from plate to plate. In yet another alternative preferred embodiment each plate can have multiple gaps such that a portion of the algal biomass drops to the plate below through each gap, creating a more turbulent waterfall than would a single gap in each plate. In a further alternative preferred embodiment, the plates have holes of any suitable size and shape in place of gaps through which biomass passes from one plate to the one below. In another further alternative preferred embodiment, each plate is smaller than the plate below such that the algal biomass flows off the lower end of one plate onto the exposed upper end of the plate below.

The PBR 105 is preferably configured as a continuous flow system. Referring again to FIG. 1, new algal biomass 813 is continually introduced into the PBR 105 via a valve 815 and an air seal 817. The flow rate of new biomass is substantially equal to the bleeding of extracted biomass 819 out of the bioreactor 105 via a seal 821 and the action of a pump 823. The pump 823 optimally lifts the algal mass in a manner that minimizes the shearing stress on the algae cells such as a lifting mechanism, screw, bucket belt, etc. In an alternative embodiment, the PBR is configured for batch processing.

In preferred embodiments the angled plates have surface features that promote turbulence in the biomass flow and create areas where the thickness of the algal biomass layer will be less than in other areas. The surface features include indentations, corrugations, pockmarks, grooves, notches or the like.

Figure 3:
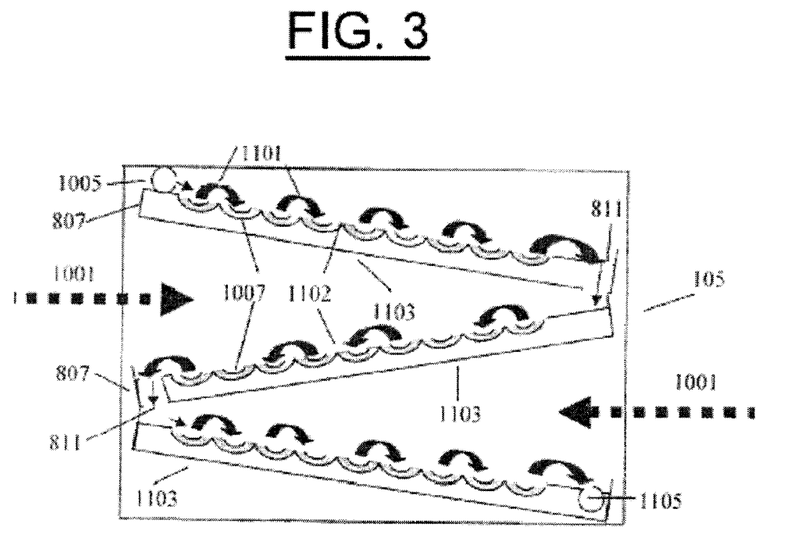

Referring now to FIG. 3, an embodiment is shown wherein algal biomass solution 1101 flows out of a conduit 1005 with regular holes in its side and fed by an inlet valve (not shown). The mass flows from the conduit 1005 and cascades down the plurality of algal production plates 807 until reaching a bottom conduit, with suitable capture openings, from where it is pumped out of the PBR 105 via an outlet port (not shown). The turbulent cascading of the algal biomass 1101 is facilitated by the surface features such as pockmark indentations 1007 in the algal production plates 807 (shown only for the sake of convenience as being equal and sequential). These indentations 1007 are distributed in a manner known in the art that maximizes the turbulent mixing of the biomass 1101 and facilitates optimal light/dark cycles for the algal cells and have shapes that include sinusoidal, spherical, elliptical and polygonal. The arrangement may be such as to form a regular array, such as a rectangular array, a hexagonal array. Alternatively, the pattern can be random or a complex mosaic with repeating and non-repeating combinations of angular and translational symmetries. In addition, the surface features may vary in size and shape so that a given bolus of medium may run over multiple shapes and sizes of surface features as it cascades down the plates 807.

When the flowing microalgal cells are in the indentations 1007 the biomass depth is greater than the depth at cusps 1102. The high density of the algal biomass as described in previous embodiments causes the part of the biomass suspension 1101 that is temporarily resident in the indentations 1007 to be largely opaque to the reflected and optionally concentrated solar radiation sunlight 1001. The thinner portions of the biomass 1101 layer overlying the cusps 1102 is more transparent, thus helping to ensure that all the algae are exposed to radiation as well as ensuring vigorous mixing. The mixing also helps to ensure that no algae are blocked from being exposed. With the high algae density (at least 20 grams per liter) of the preferred embodiment, the mixing and surface variegation are more important due to the consequent relative opacity. By way of example, surface features and plate angles may be chosen so that the biomass depth varies between 20 mm and 2 mm as it moves between lower (indented) portions and higher (cusp) portions.

Angled plates 807 for algal production may be made of any environmentally stable and rigid material such as metal, plastic, glass or ceramic. In a preferred embodiment, the plates 807 are substantially transparent to visible light in order to allow solar radiation 1001 to reach the turbulently cascading biomass flow 1101 from below as well as from above. An example of a suitable transparent material is Plexiglas®. In another preferred embodiment, the underside 1103 of the plates 807 has a reflective layer or coating which allows the solar radiation 1001 impinging on the underside 1103 of a plate 807 to be reflected onto the top side of the plate below where it can effect photosynthetic growth in the biomass 1101 flowing thereupon. For example, a plastic plate 807 may have a metal film deposited thereon or a polished metal support attached to it.

The preferred method of effecting a downward flow of biomass within a PBR is to allow the biomass flow with gravity down each angled plate and from plate to plate. In addition, a PBR includes pipes (or tubes, conduits, or the like) for ingress thereto and egress therefrom of biomass, and optionally valves, seals and/or pumps, preferably computer-controlled, for regulating the flow of biomass into and out of the PBR. In alternative embodiments, methods of effecting a downward flow of biomass within a PBR also include pumping and siphoning, and a stirring or sweeping mechanism can be added at angular junctions to avoid clogging by biomass.

In some embodiments, algal biomass flows once through the PBR as described in preceding embodiments and is evacuated from the PBR for harvesting, milking, or downstream processing. In other embodiments, the algal biomass is recirculated within the PBR at least once in order to increase biomass growth beyond what is possible in a single pass through the PBR. Recirculation can be effected by pumps and a recirculation channel, pipe or conduit from the lower end of the bottom plate to the top of the PBR in proximity to where biomass enters the reactor. In this case it is possible to control the rate of recirculation to extract a predetermined fraction of the circulating biomass in each given period of time while adjusting the flow at the inlet of the reactor to maintain a constant volume or mass of biomass within the reactor.

In a preferred embodiment, the at least one substantially transparent wall of a PBR is coated with a material capable of attenuating, blocking, absorbing, reflecting or filtering out the infrared portion of the spectrum in order to reduce the potential heating effect of infrared radiation on the biomass in the PBR. Such a material can include a dichroic or dielectric filter, fumed silica, dyed glass or other infrared-blocking material such as is known in the art. In an equally preferred embodiment, the wall itself may be constructed of a material that is substantially transparent to visible light but which does not transmit infrared radiation toward the intended receiving surfaces.

In another preferred embodiment, spectrum-selecting materials are used as part of or in conjunction with, the transmitting portion of the external walls 803 to select specific bands of the visible spectrum that enhance production of the algal biomass during the various stages of its growth. Alternatively, the spectrum-selecting properties can stem from the choice of materials used for the external wall itself. In both cases, spectral selection may be desirable. For example, red light enhances algal growth in certain species, while blue light enhances the metabolism of secondary carotenoids. The transparent wall or walls of the PBR may be configured by means of selecting a coating or construction material or method to achieve this spectrum selection in the same way as described above with respect to filtering out infrared radiation.

Figure 9A:
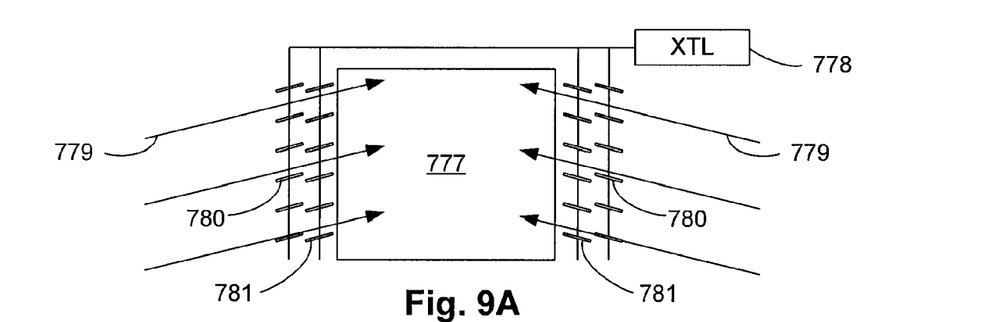
FIGS. 9A and 9B show a receiver with selectable filtration for impinging concentrated light.
Figure 9B:
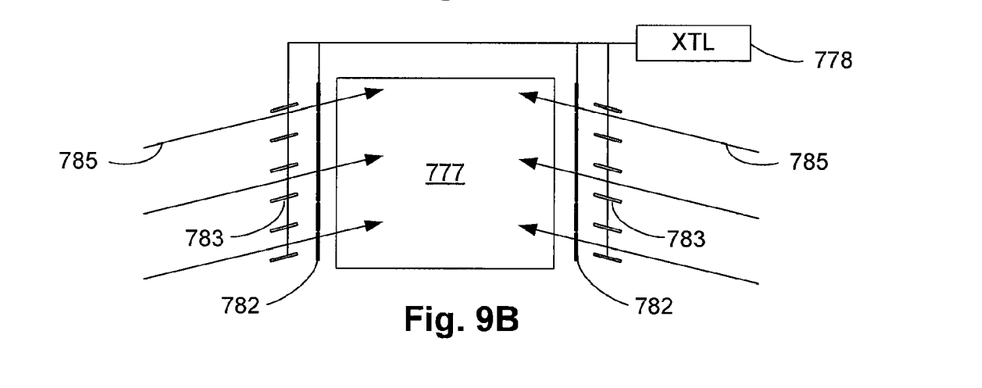

In another embodiment the transparency of at least one wall of a PBR 777 can be adjusted in accordance with the quality of quantity of incident solar radiation 779 or other meteorological conditions such as temperature or relative humidity. Referring now to FIGS. 9A and 9B, movable filtering or blocking vanes 780 or louvers can be used to control the total incident radiation or to selectively vary the opacity to selected wavelengths. In an embodiment, the vanes 780 are made of a selectively transmissive material to, for example, attenuate certain wavelengths more than others to produce a transmitted spectrum which is diminished in undesired wavelengths. More than a single set of vanes can be provided, as indicated by an additional set of vanes 781, to provide an alternative or cumulative attenuation effect, in cooperation with vanes 780, or full (using closed opaque vanes) or partial occultation (using partially blocking vanes or partially closed vanes) of the incoming radiation 779 depending on the desired conditions and materials of the vanes. For example, if radiation 785 at a different time or atmospheric condition tends to have a higher proportion of infrared, the vanes may adjusted to provide filtering of IR components as indicated by closed vanes 782. The control functions may be provided by a suitable controller 778 with appropriate sensors and/or a clock.

Alternatively a selectively-transmissive gas, such as CO2, can be injected into a space between two glass plates. Any of these can be used with a wavelength-selective material to compensate for the ratio of wavelength range impinging as a result of humidity, time of day, or other effects such as air pollution. The parameters could be measured or predicted and used to introduce one or more selective filter layers over the aperture of the receiver.

In an embodiment, a PBR is hermetically sealed and includes a valve for ingress of a gas. In an example the gas is $O_2$ or $CO_2$. The PBR can be configured to allow different gases ingress at different times, in accordance with the requirements of the biomass being grown at the time. The PBR can also be configured to bubble a gas through a biomass to enhance biomass production. In another embodiment, a PBR includes a valve for egress of an exhaust gas. The exhaust gas is optionally separated and reused for biomass growth or as a fuel. In yet another embodiment, a PBR includes a valve through which nutrients are introduced into the reactor for heterotrophic or mixotrophic growth. The nutrients are selected from sugars, sugar alcohols, and partially treated hydrocarbon-containing waste materials such as wastewater, industrial effluent or sewage.

Figure 4:
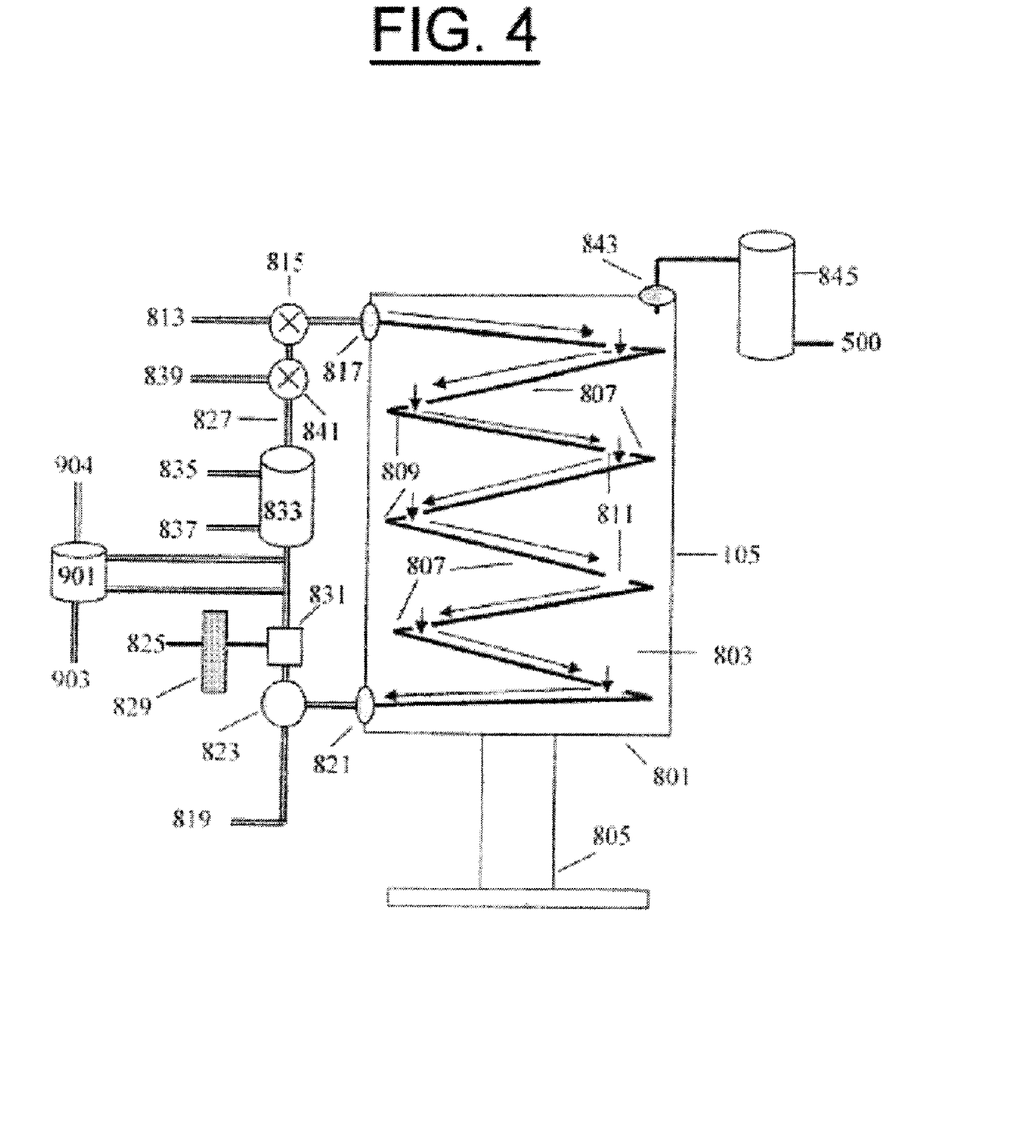
FIG. 4 is an elevation-view cross section of a photo bio-reactor, with additional and optional system elements shown schematically.

Referring now to FIG. 4, the reactor of FIG. 1 is shown with gas ingress and egress piping in accordance with an embodiment. Carbon dioxide gas is optionally introduced 825 into the recycling stream 827 after filtration 829 through a gas-liquid mixing chamber 831. In an embodiment the carbon dioxide 226 can be supplied in full or in part from the waste gases from a power plant (not shown). The circulating biomass in the recycling stream 827 is cooled via a heat exchange unit 833 with chilled water entering 835 from a chilling unit (not shown) and heated water 837 returning to the chilling unit (not shown). Fresh nutrients 839 are introduced to the recycling stream 827 via the valve 841. In the preferred embodiment the oxygen that is expired during the photosynthetic growth cycle of the algae is released from the PBR 105 via an air seal 843. The oxygen is separated from other gases via a gas separation unit 845 such as are known in the art. The oxygen stream 500 can be transferred, for example, to a combustion chamber of a gas turbine or other engine (not shown) or used for other industrial purposes.

According to an embodiment, a biomass storage facility means is provided in fluid communication with a PBR. The biomass storage facility is used for storing a photosynthetic biomass during non-daylight hours to allow growing a non-photosynthetic biomass (instead of the photosynthetic biomass) in the same PBR during non-daylight hours, or for storing a non-photosynthetic biomass during daylight hours. According to the embodiment, a liquid is used to flush the reactor reduce the possibility of cross-contamination of the two biomasses. The liquid for flushing may enter and exit through the same piping as the biomass, or through piping provided specifically for that purpose.

According to another embodiment, a proportion of the biomass is diverted from the internal circulation stream to an external vessel or chamber and subsequently returned after a substance of value is extracted. For example, astaxanthin may be milked from the microalga *Haematococcus pluvalis*, beta-carotene may be milked from the microalga *Dunaliella salina*, or lipids may be milked from various microalgal species, all with retention of viability of the biomass. In another embodiment, a proportion of the biomass is diverted from the PBR and not returned after the substance of value is extracted. In yet another embodiment, the substance of value is a lipid which is subsequently chemically converted to produce biodiesel. In a further embodiment, a fraction of the biomass remaining after extraction of a substance of value is recovered, dried and chemically converted to a fuel such as methane, methanol, ethanol or butanol.

In an embodiment, excess heat is recovered from the flowing media in, or flowing out of, the PBR and used in an industrial process or in the production of electricity. Alternatively, heat transfer cooling channels in the plates or channels acting as turbulators overlying the plates may be provided to remove heat from the flowing media and the surrounding air/gas.

In other embodiments, a photo bio-reactor system (PBRS) includes at least one PBR and a plurality of tracking heliostats and uses reflected and optionally concentrated and/or filtered solar radiation to grow a biomass in the PBR. In order to distribute light most effectively and additionally to avoid blocking and shadowing, the heliostats are optimally arranged in a rhomboid or conic array where the PBR is located at a point either in the array itself or in the center of the array.

Figure 5:
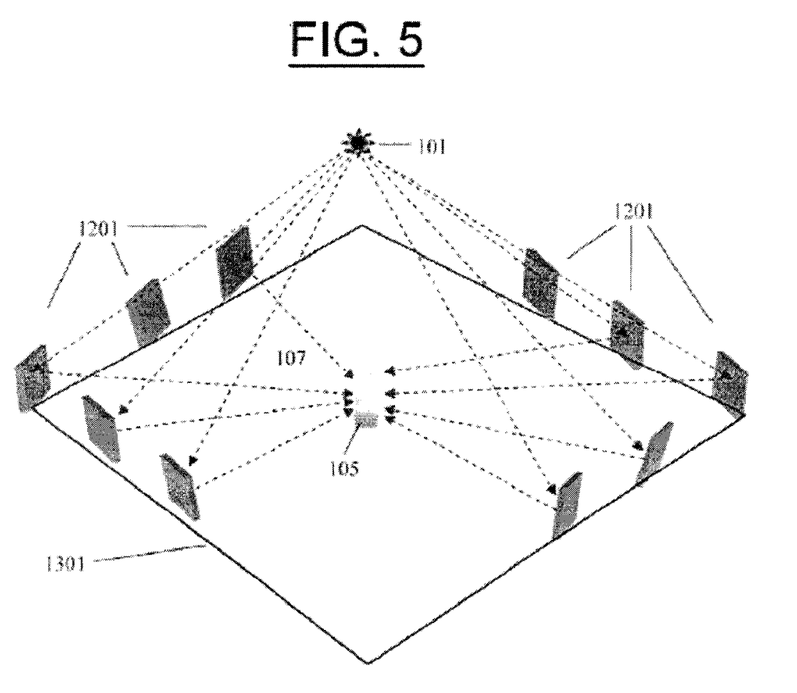
FIG. 5 is a diagrammatic representation of a photo bio-reactor system including a photo bio-reactor system and an array of tracking heliostats.

FIG. 5 shows a PBRS in which the PBR is at the center of an array of heliostats receiving concentrated light from two sides. The array comprises a diamond 1301 with a PBR 105 placed at the center of the diamond 1301 and a plurality of two-axis tracking heliostats 1201 placed around the edges of the diamond 1301. The arrangement of a plurality of heliostats 1201 in the shape of a diamond 1301 allows for the optimal collection of sunlight for such a system with minimum shadowing of one heliostat 1201 upon another. Furthermore this arrangement allows for continuous collection of sunlight from sunrise to sunset. It is understood that the number of heliostats 1201 depicted is by way of example only. Light from the sun 101 is reflected by the heliostats 1201 directly into the PBR 105. This method allows for optimizing the amount of sunlight available for photosynthesis in high-density algal biomass, and the amount of solar flux concentrated on the PBR 105 can be kept substantially constant during the passage of daytime hours. This is achieved, inter alia, by selectively orienting the plurality of heliostats 1201 to be either shining onto the solar bioreactor 105 or not shining into the PBR 105. For example, in the early morning and in the late afternoon all the heliostats 1201 can be brought into alignment so as to reflect maximum sunlight directly into the PBR 105, while during the midday hours some of the heliostats 1201 are taken off line in order to reduce the total amount of sunlight reaching the PBR 105.

Figure 6:
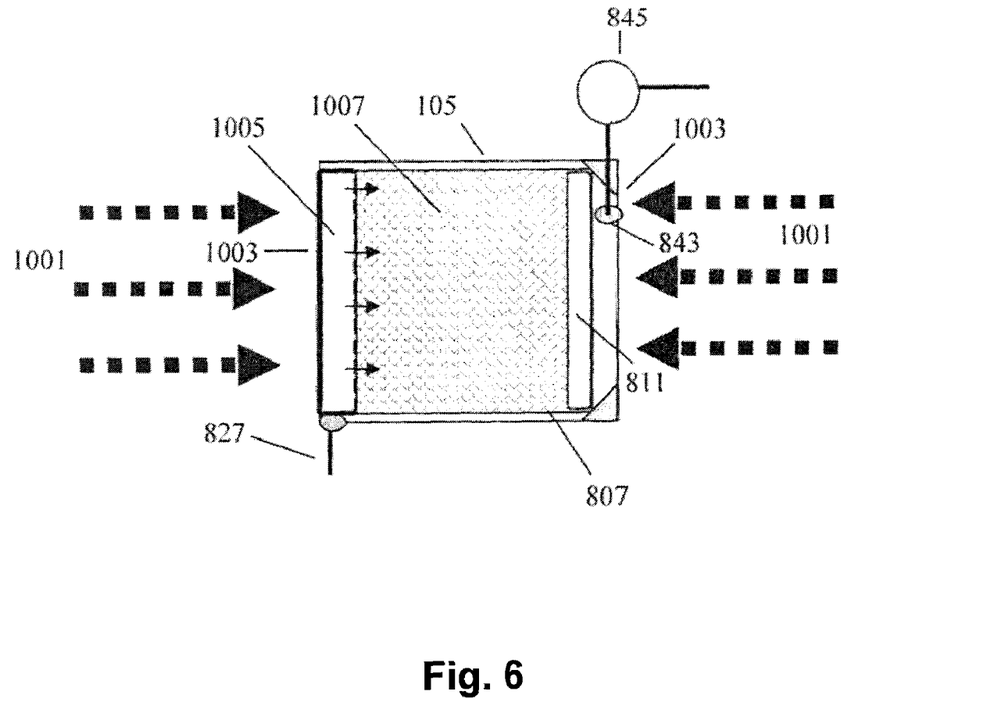
FIG. 6 illustrates a cut away top view of the solar bioreactor showing the algal production plate.

Referring now to FIG. 6, an embodiment the solar bioreactor 105 receives solar irradiation 1001 from the solar heliostats or other concentrator (not illustrated in this figure). High intensity sunlight 1001 enters the solar bioreactor 105 via the transparent walls 1003 and strikes algal production plates 807. Algal biomass continually enters the solar bioreactor 105 via a recycling system 827 and into a perforated trough or pipe 1005. The fluid flows through the holes in the trough or pipe 1005 in a manner that allows for an even distribution of liquid across the top of the algal production plates 807. The algal production plates 807 are, as explained, surface-augmented, for example with indentations 1007 that set in manner that creates turbulence and efficient mixing of the algal fluid biomass as it descends towards the lower end of the algal production plates 807. In this manner, and as is known in the art, the algal cells exchange turns near the surface and in and out of light/dark in the layer thereby allowing high efficiency and uniform photon absorption by the photoreceptors in the algal cell and high efficiency for the photosynthetic pathway. The algal fluid mixture cascades down the algal production plate 807 until reaching the waterfall gap 811 whereupon the algal biomass falls down to the upper edge of the algal production plate (not shown) immediately below this algal production plate 807. Gases are released from the solar bioreactor 105 via the port 843 and the oxygen resulting from the photosynthetic pathway is separated via a gas separation unit 847.

Figure 7:
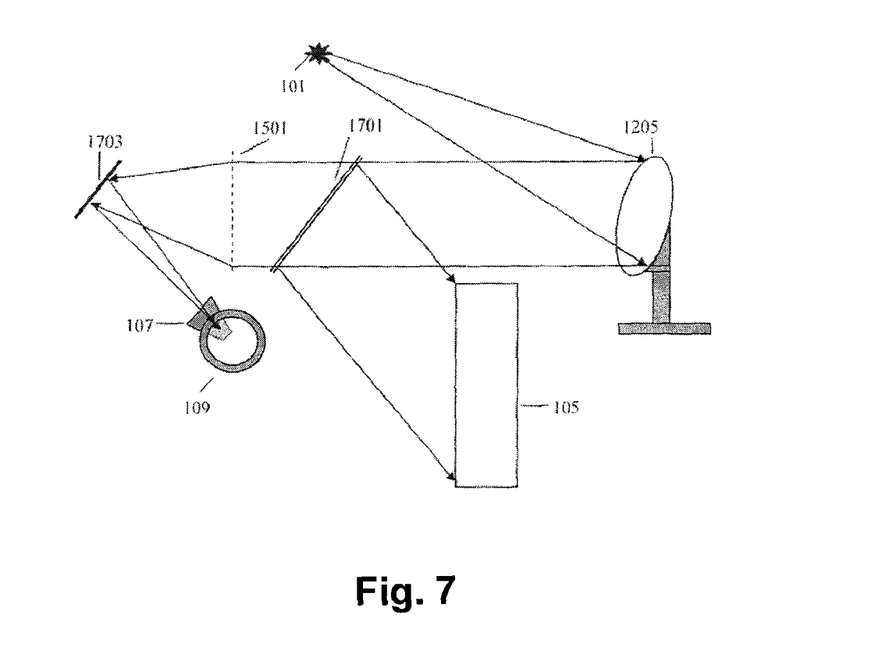
FIG. 7 illustrates an embodiment of a solar collection system in which a bio reactor and the heat exchange system receive light from a single heliostat reflector or array of reflectors, such as heliostats.

Referring now to FIG. 7, to illustrate the use of a selective transmitter/reflector as mentioned above, an alternative embodiment of the light collection system involves a two dimensional tracking heliostat 1205 reflecting light from the sun 101 onto a half mirror 1701. Such a half mirror 1701 includes, by way of example, a half mirror 1701 which is transparent and reflective to the entire spectrum of the incident light from the heliostat 1205, and a half mirror 1701 in which a selective pan of the spectrum is transmitted and a selective part of the spectrum is reflected such as a cold mirror and a hot mirror as is known to one skilled in the art. The reflected light is directed from the half mirror 1701 onto the transparent side of a solar bioreactor 105. The transmitted light from the half mirror 1701 strikes a focalizer 1501. The focalizer 1501 is transparent and can be, by way of example, flat, such as a Fresnel tens and curved, such as a solid optical lens. The focalizer 1501 can have graduated surfaces that allows light from a plurality of heliostats 1201 at different angles to the focalizer 1501 to be focused onto a single focal area. The partially focused light from the focalizer strikes a secondary mirror 1703 that sends the light into a focal area within a heat exchange device 107. The heat from the focused light is transferred by the heat exchange device 107 to a cooled insulated heat transportation pipe 109 that transports the heat to a power plant III. Furthermore it is understood by one skilled in the art that such an arrangement involving a half mirror 1701, a focalizer 1501, and a secondary mirror 1703 can be used within an array of heliostats to illuminate simultaneously a solar bioreactor 105 and provide energy to a heat exchange device 107. Such an arrangement may employ a half mirror 1701, a focalizer 1501, and a secondary mirror 1703 used with an array of heliostats to illuminate simultaneously a solar bioreactor 105 from two sides and provide energy to a heat exchange device 107.

Figure 8:
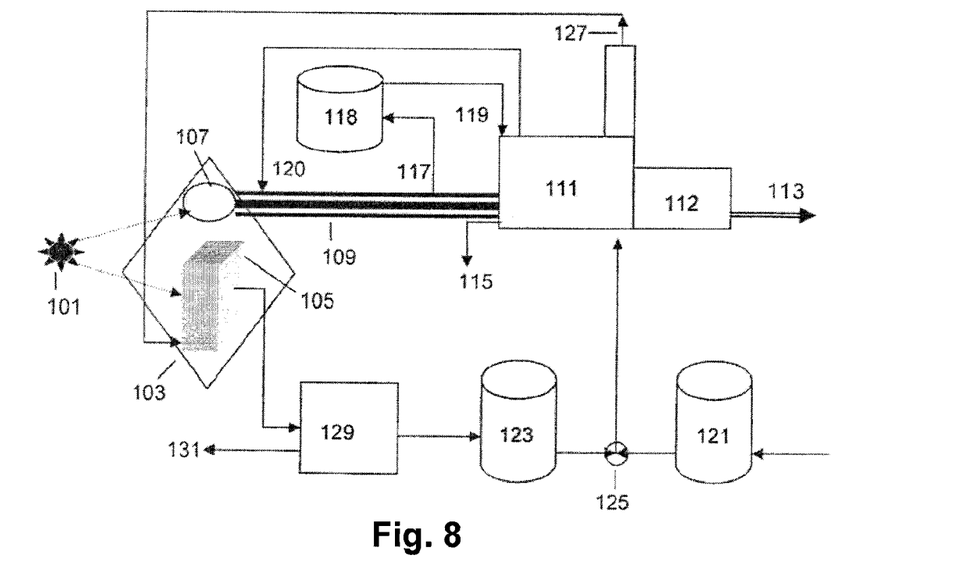
FIG. 8 illustrates a flow diagram of a preferred embodiment of the overall layout of a solar cogeneration system in which solar flux is supplied to both bio reactors, for the purposes of growing algae, and to a heat exchange system for the purposes of generating electricity and steam.

Referring to FIG. 8, solar flux 101 is concentrated within a solar field 103 consisting of such optical components including reflectors, mirrors, half-mirrors, hot-mirrors, cold-mirrors and lenses, so as to provide simultaneously, at least a uniform, multi-solar irradiation for an algal bioreactor 105 and a high intensity light beam directed into a heat exchange cavity 107 for the purposes of heating a fluid heat transport medium. It is understood that the solar field may provide the concentrated light to the reactor and to the heat exchange cavity in series or in parallel. The heat exchange cavity 107 transforms the irradiated heat into convective heat within a fluid medium that includes but is not limited to oil, steam, air, air/carbon mixture and molten salts. The fluid medium transfers the heat via an insulated and cooled piping system 109 to a power plant 111 where the heat is used to power a turbine such as a combined cycle turbine, that turns a generator 112 to produce electrical output 113.

Other cogenerational outputs 115 include steam for purposes that include heating for co-located facilities and steam sterilization of the algal bioreactor 105, and energy for powering cooling systems for the algal bio reactor 105. A further source of energy is derived from the accumulated heat in the cooling medium of the piping system 109. Such a cooling medium includes high boiling point oils, super cooled gases and cooled liquids. The hot cooling medium 117 is circulated to an insulated energy storage unit 118. The hot medium is circulated to the power plant 111 where it is used to provide energy for second tier energy production such as a steam turbine and steam generation.

The cooled cooling medium is re-circulated 120 to the insulated and cooled piping system 109. Supplementary energy is supplied by alternative fuel sources including but limited to natural gas 121 and biomass fuel 123 such as methane derived from the algal bio reactor 105. The proportions of such supplementary fuels 121, 123 are determined by the control unit 125. The carbon dioxide exhaust 127 from the combustion of the supplementary fuels 121, 123 is directed to the algal bioreactor 105 as non-organic carbon source for the photosynthetic growth of the algal biomass.

The biomass derived from the algal bioreactors is processed in the downstream processing facility 129. This facility 129 includes such processes as concentration of biomass, cell rupturing, extraction of algal contents, centrifugation of biomass, spray drying of whole algal cells, formulation of cell contents, conversion of biomass and bio-organic residues into combustible bio fuels. The non-fuel output 129 from the downstream processing facility 127 includes but is not limited to high value chemicals such as astaxanthin, β-carotene, coenzyme Q10 arachadonic acid, whole cell Chlorella, whole cell Spirulina, ruptured cell Haematococcus, algal-based foods.

In a preferred embodiment, heliostats in the heliostat array are controlled by a computerized control system, which directs the aiming and tracking of the individual heliostats, including directing heliostats not to reflect radiation onto the PBR during hours of excess insolation. In another preferred embodiment, the PBR is controlled by a computerized control system which is optionally in data communication with the control system of the heliostats. The control systems use predictive control based on historical patterns of solar radiation, preferably in conjunction with real-time feedback from measurements of instant solar radiation and other meteorological conditions, temperature measurements internal to or external to the PBR, or gravimetric measurements of algal biomass. The control systems function individually or in tandem to optimize the concentration and distribution of solar flux that reaches the PBR with the optimization goals being even distribution on the angled plates inside the PBR, i.e., avoiding hot spots and cold spots, and also achieving and maintaining a predetermined level of solar flux throughout the daylight hours. The predetermined level of solar flux may vary among microalgal species but in exemplary embodiments is less than a full sun or approximately 1000 Watts per square meter. Preferably, the flux is between one-third of a sun and two-thirds of a sun or about 300 to 700 Watts per square meter. In a more preferred embodiment the predetermined level of solar flux is half a sun (approximately 500 Watts per square meter of angled plate area). Alternatively, the control systems function individually or in tandem to optimize temperature for biomass growth. In an especially preferred embodiment, the control systems function individually or in tandem to achieve and maintain a level of solar flux that maximizes biomass growth.

In other embodiments, a PBRS includes additional elements such as secondary reflectors or concentrators (such as a fresnel lens, for example) interposed between heliostats and a PBR in order to optimize the distribution of solar flux reaching a PBR. In still other embodiments, a PBRS also includes a spectrally selective element for filtering or splitting the spectrum of light reflected by heliostats, before the light reaches the PBR in order to filter out infrared radiation or select a portion of the spectrum known to enhance productivity of the algal biomass. In further embodiments, a PBRS also includes a diffusive element for diffusing reflected light reaching a PBR and thereby increasing the uniformity of solar flux on algae-producing plates within.

In yet another embodiment, a PBR is provided having an aspect ratio compatible with the aspect ratio of the heliostats in a heliostat array. By way of example only, such an aspect ratio would be 6.5:6:5. For example, a solar bioreactor could have dimensions 6.5 meters in height, 5 meters in length, and 6 meters in width. In a further embodiment, a PBR is provided atop a base or tower with a height consistent with the height of heliostats in a heliostat array.

In another embodiment, an integrated solar system includes a PBRS as described in the preceding embodiments and at least one solar receiver which converts solar radiation reflected by heliostats to a useful form, such as by photovoltaic conversion or by heating a fluid for use in an industrial process or in the production of electricity. The heliostats which track solar radiation to the receiver may be part of the heliostat array of the PBRS and may include additional heliostats.

Certain features of this invention may sometimes be used to advantage without a corresponding use of the other features. While a specific embodiment of the invention has been shown and described in detail to illustrate the application of the principles of the invention, it will be understood that the invention may be embodied otherwise without departing from such principles.

The invention claimed is:

1. A photobioreactor system, comprising:
   a receiver, a solar concentrator, the receiver being positioned to receive concentrated sunlight from the concentrator;
   an array of flat members with respective first surfaces, the flat members forming a cascade with each being positioned and oriented to receive substantially one sun or less of solar flux level or less than 1000 Watts per square meter;
   a fluid conveyance configured such that, by gravity, a fluid received by a first of the flat members runs down the first flat member first surface and is conveyed to a second of the flat members and runs down the second flat member first surface,
   wherein the solar concentrator includes an array of heliostats surrounding the receiver.

2. The system of claim 1, wherein the receiver includes a recirculating fluid transport device that partially recirculates fluid from the bottom back to the top so that the fluid flows down the cascade of flat members and partially conveys fluid away from the receiver.

3. The system of claim 1, wherein the receiver includes a light transmitting wall.

4. The system of claim 1, wherein the receiver includes a light transmitting wall portion that attenuates selected optical wavelengths.

5. The system of claim 1, wherein, for each flat member, a second surface, located behind the first surface, has a reflective coating.

6. The system of claim 1, wherein the flat members include cooling channels.

7. The system of claim 1, further comprising cooling channels aligned with the first surfaces.

8. The system of claim 1, wherein the first surfaces have augmentations and orientations such that liquid may pool in recesses at depths of no more than 20 mm.

9. The system of claim 1, wherein the fluid conveyance includes a vessel with a gas supply.

10. The system of claim 1, wherein the fluid conveyance includes a vessel with a gas supply and a gas outlet.

11. The system of claim 1, wherein the fluid conveyance is coupled to a milking apparatus for removing a substance from algae.

12. The system of claim 1, wherein the fluid conveyance conveys fluid consisting substantially of algae and liquid media where a dry mass of algae is 25 g per liter of the fluid.

13. The system of claim 1, wherein the solar concentrator is spaced from the receiver such that at least a portion of the light path between the concentrator and the receiver is through free space.

14. The system of claim 1, wherein the flux level is between ⅓ and ⅔ of a sun or between 300 and 700 Watts per square meter.

15. The system of claim 1, wherein the flux level is about a half sun or about 500 Watts per square meter.

16. The system of claim 1, wherein the flat members are oriented at between 5 and 20 degrees from the horizontal.

17. The system of claim 1, wherein the flat members are made of polymeric material.

18. The system of claim 1, wherein the receiver has another array of flat members.

19. A photobioreactor system, comprising:
a receiver, a solar concentrator, the receiver being positioned to receive concentrated sunlight from the concentrator;
an array of flat members with respective first surfaces, the flat members forming a cascade with each being positioned and oriented to receive substantially one sun or less of solar flux level or less than 1000 Watts per square meter;
a fluid conveyance configured such that, by gravity, a fluid received by a first of the flat members runs down the first flat member first surface and is conveyed to a second of the flat members and runs down the second flat member first surface; and
a control system configured to control the solar concentrator to regulate an intensity of flux falling on the flat member first surfaces over the course of time to maintain at least one target flux level,
wherein the solar concentrator includes a ring of heliostats in the shape of a rhombus surrounding the receiver.

* * * * *

UNITED STATES PATENT AND TRADEMARK OFFICE
CERTIFICATE OF CORRECTION

PATENT NO. : 8,003,379 B2
APPLICATION NO. : 11/832201
DATED : August 23, 2011
INVENTOR(S) : Arnold J. Goldman, Michael Kagan and Yuri Kokotov It is certified that error appears in the above-identified patent and that said Letters Patent is hereby corrected as shown below:

On the Title Page, insert the following data:

Item --(30) Foreign Application Priority Data

Apr. 6, 2007    (WO) .................................. PCT/US07/66195--

Signed and Sealed this
Sixth Day of December, 2011

David J. Kappos
*Director of the United States Patent and Trademark Office*